United States Patent [19]

Evans

[11] Patent Number: 5,543,161
[45] Date of Patent: Aug. 6, 1996

[54] YEAST STRAIN

[75] Inventor: Robert J. Evans, Bridport, United Kingdom

[73] Assignee: Burns Philp & Company Limited, Sydney, Australia

[21] Appl. No.: 378,594

[22] Filed: Jan. 26, 1995

Related U.S. Application Data

[63] Continuation of Ser. No. 208,577, Mar. 11, 1994.

[30] Foreign Application Priority Data

Mar. 12, 1993 [AU] Australia .................. PL7754

[51] Int. Cl.$^6$ .................. C12N 1/18; A21D 8/04; A21D 10/00
[52] U.S. Cl. .................. 426/62; 426/19; 435/255.2
[58] Field of Search .................. 435/255.2, 252.2; 426/62, 19

[56] References Cited

FOREIGN PATENT DOCUMENTS

| | | |
|---|---|---|
| 2055052 | 5/1992 | Canada . |
| 15512733 | 3/1990 | U.S.S.R. . |
| 9301724 | 2/1993 | WIPO . |

*Primary Examiner*—Herbert J. Lilling
*Attorney, Agent, or Firm*—Rothwell, Figg, Ernst & Kurz

[57] ABSTRACT

The present invention relates to new baker's yeast *Saccharomyces cerevisiae* strains which have improved temperature tolerance and/or keeping quality. An example of such a strain has been designated YTTS and deposited AGAL and accorded accession No. N93/10504.

3 Claims, No Drawings

YEAST STRAIN

This is a continuation of application Ser. No. 08/208,577, filed Mar. 11, 1994.

The present invention relates to a bakers yeast *Saccharomyces cerevisiae* which has improved temperature tolerance and keeping quality.

Bakers yeast is typically produced by a fed-batch fermentation process at temperatures up to about 35° C. Above this temperature both yield and baking performance are usually compromised. Unfortunately, considerable heat is generated during fermentation and the fermentors must be cooled to maintain optimum conditions for yeast growth. Due to the large culture volumes involved in commercial fermentations (typically around 100,000 liters) cooling can represent a substantial component of overall production costs, particularly in countries which experience high sumer temperatures. A strain which can tolerate even small increases in production temperature, without significant loss of baking performance, is therefore desirable.

Another important feature in a bakers yeast product is its keeping quality. This is the ability of the product (at 17–34% solids) to retain its baking activity during a period of storage. Depending on the availability of bakery refrigeration, the conditions of such storage may range from around 4° C. to in excess of 25° C.

The present inventor has produced a bakers yeast *Saccharomyces cerevisiae* strain which is improved in respect to both temperature tolerance and storage characteristics. A sample of this yeast strain, designated YTTS, was deposited with Australian Government Analytical Laboratories (AGAL) at 1 Suakin Street, Pymble, New South Wales 2073, Australia on 11 Mar. 1993 and was accorded Accession No. N93/10504.

Accordingly, in a first aspect the present invention consists in a baker's yeast *Saccharomyces cerevisiae* strain, the strain being characterised in that there is less than a 12% decrease in yield of grams of wet yeast at 30% solids per 100 g total reducing sugar when the strain is brewed at 37° C. in comparison to brewing at 30° C.

In a second aspect the present invention consists in a baker's yeast *Saccharomyces cerevisiae* strain, the strain being characterised in that the strain retains at least 90% of its activity in plain dough at 37° C. when brewed at 37° C. in comparison to when brewed at 30° C.

In a third aspect the present invention consists in a baker's yeast *Saccharomyces cerevisiae* strain, the strain being characterised in that the strain brewed at 30° C. retains at least 95%, and preferably at least 97%, of its activity after storage for 21 days at 4° C. at 24.5% solids.

The present invention also relates to baker's yeast *Saccharomyces cerevisiae* which have more than one of the characteristics specified in the first, second and third aspects of the present invention.

In a preferred embodiment of the present invention the *Saccharomyces cerevisiae* strain is strain YTTS (AGAL N93/10504).

In a fourth aspect the present invention consists in a fresh or dry bakers yeast composition, the composition being characterised in that it includes bakers yeast of the first, second or third aspect of the present invention.

As stated above a *Saccharomyces cerevisiae* strain of the present invention, designated YTTS, was deposited with AGAL. In order that the nature this strain may be more clearly understood its performance was compared with another yeast, Strain A (also deposited with AGAL, Accession No. N94/8029), representative of those currently used in markets where temperature tolerance and keeping qualities are important. This comparison is followed by a list of further characteristics of strain YTTS.

Production and Preliminary Assessment of Hybrid Yeast Strains

Hybrid yeast strains were produced using classical methods of the sort described in "Yeast Genetics—a manual of methods" (Spencer J. F. T., Spencer D. M. and Bruce I. J., Springer-Verlag, Berlin Heidelberg, 1989).

In a typical procedure strains of diploid or higher ploidy are subjected to manganese mutagenesis (Putrament A., Baranowska H. and Prazamo W., Molec. Gen. Genet., 126: 357–366, 1973) to recover mitochondrial antibiotic resistance mutants. The strains are subsequently sporulated by incubation at 20° C. on a solid medium comprising 0.5% w/v potassium acetate and 1% agar. After 5–6 days asci are harvested and matable forms recovered by random spore isolation, using the ether method of Dawes and Hardie (Molec. Gen. Genet., 131: 281–289, 1974) to kill unsporulated vegetative cells. Spores are separated from any remaining vegetative cells by mixing the suspension with an equal volume of mineral oil then allowing the spores to partition into the oil phase. They are subsequently germinated by spreading to nutrient agar plates. The mating type of the resulting haploid colonies is determined by agglutination with tester strains and their resistance to selective markers confirmed. Novel hybrids are formed by crossing haploids carrying complementary markers using the drop overlay method (Spencer et al., op cit, p 4–5). Selection against un-mated cells is on 4% glycerol YEP plates supplemented with the appropriate antibiotics. Hybrids are identified by their ability to sporulate and by the presence of both parental markers.

Baking performance of hybrids is predicted in the laboratory by an adaptation of the thin flour dough method of White (p 403, in *Yeast Technology*, Chapman and Hall, 1954). In this test 170 mg of wet yeast (50 mg dry weight) is suspended in 30 ml of 0.33 mM NaCl then mixed into 28 g of flour for 1 minute. The 50 ml thin dough is transferred to a 100 ml measuring cylinder then incubated at 30° C. The activity of a novel hybrid relative to a control strain is determined by noting the change in volume of the doughs at 30 minute intervals. Strain YTTS was identified as having commercial potential on this basis and was further characterised by comparison with Strain A as described below.

Assessment of Strain YTTS

Pilot scale yield, baking and keeping performance of strain YTTS were compared with Strain A.

Comparison 1

Method

Twenty liter fed-batch fermentors were inoculated at a rate of 12% (seed:final yeast) and brewing commenced at 30° C. In one series of experiments this temperature was maintained throughout the brew. In a second series of experiments the temperature was gradually increased, in 2° C. increments, from 30° C. at hour one to reach 37° C. by the end of hour five, where it was then maintained. In all cases a total of 1200 g of total reducing sugar (TRS) was used (as 50% cane/50% beet molasses). All brews were supplemented with KCl, MgSO$_4$, ZnSO$_4$, vit B1 and vit B6 and molasses feed rates controlled to produce a similar fermentation profile for both strains.

All activity tests were carried out using an SJA Fermentograph set at 30° C. or 37° C. using the dough formulations shown in Table 1. Dry ingredients were weighed into a Farinograph mixing bowl and blended for one minute. Compressed yeast was suspended in water then added to the dry ingredients, together with the salt solution. The complete dough was mixed for three minutes, reaching a final dough temperature of 30° C.

The finished dough was transferred to a standard Fermentograph tin then put into the SJA apparatus. Tests were carried out for two hours knocking the dough down after the first hour.

Baking tests were performed according to two commonly used baking processes (CDD and Sponge and Dough). In the chemical dough development (CDD) method the ingredients listed in Table 2 were assembled in a high speed mixer and mixed for six to eight minutes. The finished dough temperature was 30° C. The dough was rested on the bench for 10 minutes, scaled off at 770 g, molded then given a further 10 minutes rest time. After further molding, the dough piece was placed in a baking pan then transferred to a proofing cabinet set at 40° C. and 85% relative humidity. The time taken for the dough piece to reach a height of 120 mm (the "proof time") was noted and the dough then baked for 30 minute in a rotating oven set at 220° C. The loaf was cooled overnight and oven spring determined by subtracting proof height (120 mm) from the final height of the loaf.

The sponge and dough method differed from the CDD process in that the ingredients (Table 2) were added in two stages. The sponge stage ingredients were mixed in a high speed mixer for three minutes, achieving a final temperature of 30° C. The mixture was then fermented for four hours at 30° C. in a separate vessel, knocking down after two hours. At the end of this time the sponge mixture was transferred to a mixer and the remaining ingredients added to produce the dough stage. This was then mixed for five and a half minutes, again reaching a finished dough temperature of 30° C. The dough was rested on the bench for 10 minutes and the CDD procedure followed for the remainder of the baking process.

Results

Table 3 displays brew summaries and fermentograph activity results. The data show that the YTTS has tolerated the increase in brewing temperature (from 30° C. to 37° C.) better than Strain A, with a 10.1% loss in yield in comparison with a 14.5% loss for Strain A. Dough activities at 30° C. in all dough types were reduced for both strains as a result of brewing at 37° C. However the averaged results of the 37° C. brews when compared to 30° C. brews, reveal that, in every dough type, the loss of activity associated with growth at higher temperature is greater with Strain A than with YTTS.

Although 30° C. is often used for fermentograph testing, bakery proof temperatures are commonly higher than this. A second series of fermentograph tests were therefore performed, this time with the SJA apparatus set at 37° C. These results are also shown in Table 3. In this case, significant strain differences were noted in the losses recorded following growth at 37° C.

The fermentograph results are broadly reflected by bake test results (Table 4). In the case of the plain, chemical dough development (CDD) system, the time required for proofing is less affected for YTTS than for Strain A. There was no effect on oven spring. In terms of performance in the Sponge and Dough system, both strains behaved in a similar manner, although oven spring was less affected for YTTS.

The data of comparison 1 demonstrate that YTTS has a better tolerance to 37° C. brew temperatures than Strain A. This is manifested in terms of both yield and subsequent activity in a number of test conditions.

Comparison 2

A second important feature of YTTS is its keeping quality. The yeast samples examined in comparison 1 were subjected to three standard keeping tests. These involved conducting 30° C. plain dough activity tests before and after storage for 21 days at 4° C. The results of these analyses appear as Table 5. At both brew temperatures YTTS out-performed Strain A in terms of retention of activity on storage. This was particularly true of YTTS grown at 30° C. where a very stable product can be produced.

Strain Characterisation

Strain YTTS was characterised according to the method of van der Walt and Yarrow (pp 45–104, in *The Yeasts: a taxonomic study*, Kreger van Rij, Ed. Elsevier, Amsterdam, 1984) and Heard and Fleet (J. Appl. Bacteriol., 68: 447–451, 1990). The following characteristics were observed.

Growth in Malt Extract Broth (van der Walt and Yarrow): After 24 hours at 30° C. the cells were globose (4.9–8.8)× (6.9–9.8)μm. After 72 hours the cells measured (4.9–7.8)× (4.9–10.8)μm.

Growth on MY Agar (van der Walt and Yarrow): After 72 hours at 30° C. the colonies were circular, convex with an entire margin, cream in colour, dull and smooth.

Acetate Agar (van der Walt and Yarrow): ascospores were produced. 34% of cells had produced asci containing 1–4 globose spores after incubation for 72 hours at 25° C.

Fermentation Tests (Heard and Fleet): glucose, galactose, maltose, methyl alpha glucoside and sucrose were fermented. Melibiose, lactose, cellobiose, inulin, starch and D-xylose were not fermented.

Assimilation Tests (Heard and Fleet): galactose, sucrose, maltose, methyl alpha glucoside, raffinose, and melezitose were assimilated. L-arabinose, D-arabinose, D-rhamanose, cellobiose, melibiose, lactose, starch, erythritol, xylitol, D-mannitol, 2-keto-D-gluconate, D-gluconate, D-glucuronate, DL-lactate, succinate, citrate, ethanol, 2,3 butanediol, nitrate, nitrite ethylamine, lysine, cadaverine, creatine and creatinine were not assimilated.

Other tests (Heard and Fleet): there was no growth in the presence of 100 ppm cycloheximide or 1% acetic acid.

According to the description given by Yarrow (pp 379–395, in *The Yeasts: a taxonomic study*, Kreger van Rij, Ed. Elsevier, Amsterdam, 1984) this yeast is identified as *Saccharomyces cerevisiae* Meyen ex Hansen (1883). This identification is also supported by the data given by Barnett, Payne and Yarrow (*Yeasts: characteristics and identification*. 2nd ed., 1990).

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

TABLE 1

Fermentograph Formulations Used in Activity Tests

| Ingredients | Plain dough | 7% sugar dough | 16% sugar dough | 25% sugar dough |
|---|---|---|---|---|
| Flour | 280 g | 280 g | 250 g | 250 g |
| Sugar | — | 19.6 g | 40 g | 62.5 g |
| Bread Improver* | 1.5 g | 1.5 g | 1.3 g | 1.3 g |
| Water | 100 ml | 100 ml | 91 ml | 92 ml |
| Salt Solution (9.5% w/v) | 57 ml | 57 ml | 26 ml | 26 ml |
| Yeast (@ 30% solids) | 5 g | 5 g | 10 g | 10 g |

*Mauri Foods Bakerine Special

TABLE 2

Bake Test Formulations

| | Plain | Sponge and Dough | |
|---|---|---|---|
| Ingredient | CDD | Sponge Stage | Dough Stage |
| Flour | 2000 g | 1400 g | 600 g |
| Sugar | — | — | 160 g |
| Bread Improver | 5 g* | 12 g* | — |
| Water | 1200 ml | 900 ml | 300 ml |
| Salt | 40 g | — | 45 g |
| Yeast (@ 30% solids) | 60 g | 50 g | — |
| Vegetable Oil | 40 g | — | 5 g |
| Emulsifier (SSL) | — | — | 5 g |

*Mauri Foods Bakerex Instant
**Mauri Foods Bakerine Special

TABLE 3

Yield and Activity

| | | Average | Fermentograph Test (total ml $CO_2$ evolved per 2 hours)* | | | | | |
|---|---|---|---|---|---|---|---|---|
| | | | 30° C. Test | | | | 37° C. Test | |
| Strain | Brew Temp | Yield** | Plain | 7% sugar | 16% sugar | 25% sugar | Plain | 7% sugar |
| Strain A | 30° C. | 152 | 1240 | 1200 | 1145 | 450 | 2155 | 2000 |
| | 37° C. | 130 | 1040 | 780 | 860 | 330 | 1750 | 1478 |
| | % Loss | 14.5 | 16 | 35 | 25 | 27 | 19 | 26 |
| YTTS | 30° C. | 168 | 1300 | 1165 | 1380 | 760 | 2020 | 1850 |
| | 37° C. | 151 | 1135 | 965 | 1260 | 600 | 1925 | 1700 |
| | % Loss | 10.1 | 13 | 17 | 9 | 21 | 5 | 8 |

*All activities corrected to 30% solids and 52% protein
**Yield expressed as grains of wet yeast (@ 30% solids) per 100 g total reducing sugar

TABLE 4

Bake Test Comparison

| | | Baking Test | | | |
|---|---|---|---|---|---|
| | | Plain CDD | | Sponge & Dough | |
| Strain | Brew Yeast | Proof Time (min) | Oven Spring (mm) | Proof Time (min) | Oven Spring (mm) |
| Strain A | 30° C. | 65 | 30 | 58 | 35 |
| | 37° C. | 77 | 30 | 66 | 20 |
| | % Loss | 18 | 0 | 14 | 43 |
| YTTS | 30° C. | 62 | 30 | 58 | 35 |
| | 37° C. | 68 | 30 | 66 | 30 |
| | % Loss | 10 | 0 | 14 | 14 |

TABLE 5

Keeping Quality Comparison

| | | Activity* | | |
|---|---|---|---|---|
| Strain | Brew Temp | Initial | After 21 days @ 4° C. | Activity Retention |
| Strain A | 30° C. | 1240 ml | 915 ml | 74% |
| | 37° C. | 1040 ml | 845 ml | 81% |
| YTTS | 30° C. | 1300 ml | 1260 ml | 97%** |
| | 37° C. | 1135 ml | 1025 ml | 90% |

*Volume of $CO_2$ evolved in 2 hour plain Fermentograph test
**Average of measurements at 24.5% solids and 28.5% solids (24.5% solids-100%; 28.5% solids-95%)

I claim:
1. A biologically pure culture of a baker's yeast strain

*Saccharomyces cerevisiae* having all the identifying characteristics of *Saccharomyces cerevisiae* YTTS.

2. A dough composition comprising baker's yeast *Saccharomyces cerevisiae* YTTS.

3. The composition of claim 2, wherein the baker's yeast *Saccharomyces cerevisiae* YTTS is in dried form.

* * * * *